(12) United States Patent
Koch et al.

(10) Patent No.: US 9,676,691 B2
(45) Date of Patent: Jun. 13, 2017

(54) METHOD FOR PRODUCING INDANONE DERIVATIVES

(75) Inventors: Oskar Koch, Göttingen (DE); Dietmar Schatkowski, Einbeck (DE); William Johncock, Reinbek (DE); Christel Jahnke, Brakel (DE); Karl-Georg Fahlbusch, Höxter (DE)

(73) Assignee: SYMRISE AG, Holzminden (DE)

( * ) Notice: Subject to any disclaimer, the term of this patent is extended or adjusted under 35 U.S.C. 154(b) by 225 days.

(21) Appl. No.: 14/241,964

(22) PCT Filed: Aug. 24, 2012

(86) PCT No.: PCT/EP2012/066502
§ 371 (c)(1),
(2), (4) Date: Oct. 31, 2014

(87) PCT Pub. No.: WO2013/030110
PCT Pub. Date: Mar. 7, 2013

(65) Prior Publication Data
US 2015/0071866 A1 Mar. 12, 2015

Related U.S. Application Data

(60) Provisional application No. 61/530,139, filed on Sep. 1, 2011.

(30) Foreign Application Priority Data

Sep. 1, 2011 (EP) ..................... 11179791

(51) Int. Cl.
*C07C 45/65* (2006.01)
*C07C 49/755* (2006.01)
(Continued)

(52) U.S. Cl.
CPC ............... *C07C 45/65* (2013.01); *A61K 8/35* (2013.01); *A61Q 17/04* (2013.01); *A61Q 19/00* (2013.01);
(Continued)

(58) Field of Classification Search
None
See application file for complete search history.

(56) References Cited

U.S. PATENT DOCUMENTS

2009/0203905 A1* 8/2009 Blixt .................... C07D 211/16
544/293

FOREIGN PATENT DOCUMENTS

WO WO-2007/128723 A1 11/2007

OTHER PUBLICATIONS

Imbach, J.-L. et al. "Nuclear Magnetic Resonance spectra of derivatives of various substituted indanones and tetralones" Tetrahedron, 1967, v. 23, pp. 3931-3941.*
(Continued)

*Primary Examiner* — Mina Haghighatian
*Assistant Examiner* — Erin Hirt
(74) *Attorney, Agent, or Firm* — Polsinelli PC

(57) ABSTRACT

A method is described for producing a compound having the formula (I)

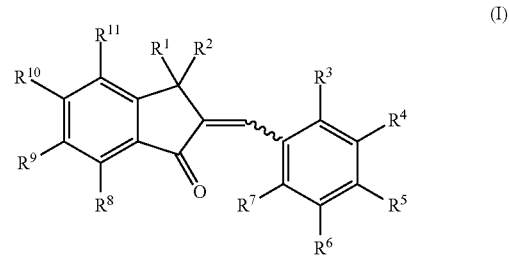

(I)

or an admixture comprising a compound having the formula (I),
having the following steps:
dissolving an indanone having the formula (II) in a solvent or in an admixture which contains a solvent, the solvent being selected from the group of solvents which form an azeotrope with water,
converting the indanone having the formula (II) with an aromatic aldehyde having the formula (III) in the presence of at least one organic base, according to the drawing:

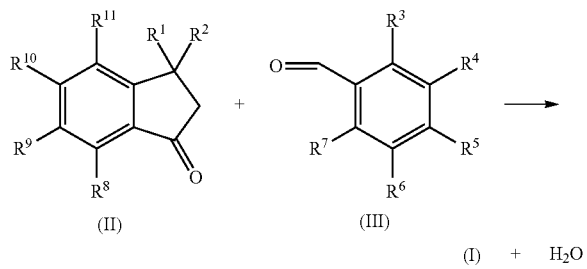

where $R^1$ and $R^2$ independently of each other signify hydrogen or a branched or unbranched alkyl group having from 1 to 12 carbon atoms and
where $R^3$, $R^4$, $R^5$, $R^6$, $R^7$, $R^8$, $R^9$, $R^{10}$ and $R^{11}$ independently of each other signify hydrogen, hydroxy or a branched or unbranched alkyl or alkoxy group having from 1 to 12 carbon atoms and
removing water formed from the reaction admixture during the conversion.
An admixture comprising a compound of the formula (I) and other components is further described.

16 Claims, No Drawings

(51) Int. Cl.
    *A61K 8/35*       (2006.01)
    *A61Q 17/04*     (2006.01)
    *A61Q 19/00*     (2006.01)
    *C07C 45/74*     (2006.01)
    *C07C 45/72*     (2006.01)

(52) U.S. Cl.
    CPC .............. *C07C 45/72* (2013.01); *C07C 45/74* (2013.01); *C07C 49/755* (2013.01)

(56) References Cited

OTHER PUBLICATIONS

The interactive Lab Primer (https://web.archive.org/web/20090204010817/http://chem-ilp.net/labTechniques/DeanStark.htm, cached wayback machine Feb. 4, 2009).*

Chemguide "LeChatelier's Principle" (https://web.archive.org/web/20021031220432/http://www.chemguide.co.uk/physical/equilibria/lechatelier.html, cached wayback machine Oct. 31, 2002).*

Purification of Laboratory Chemicals (ed. Armarego & Chai, 6th edition, 2009, pp. 7).*

Moorthy, J. N.; et al. "Highly diastereo- and enantioselective aldol reactions in common organic solvents using N-arylprolinamides as organocatalysts with enhanced acidity" European Journal of Organic Chemistry, 2009, 739-748.*

Imbach J-L, et al., "Nuclear Magnetic Resonance Spectra of Derivatives of Various Substituted Indanones and Tetralones," Tetrahedron, Elsevier Science Publishers, vol. 23, No. 1, 1967, pp. 3931-3941, XP001544619.

Imokaw G., et al., "Novel alpha-benzylidene ketone drivs.—are UV-A absorbers used as sunblocks in cosmetic prepns," WPI / Thomson, vol. 1992, No. 25, 1992, XP002667500.

International Search Report with references cited and Written Opinion under Rule 43 PCT attached to the Search Report, PCT Application No. PCT/EP2012/066502.

* cited by examiner

METHOD FOR PRODUCING INDANONE DERIVATIVES

CROSS REFERENCE TO RELATED APPLICATIONS

This application is a National Phase filing under 35 U.S.C. §371 of International Application No. PCT/EP2012/066502, filed Aug. 24, 2012, which claims priority to European Application No. 11179791.6 and U.S. Provisional Application No. 61/530,139, both filed on Sep. 1, 2011. The entire contents of each of the above-applications are incorporated herein by reference.

The present invention relates to a method for producing a compound having the formula (I)

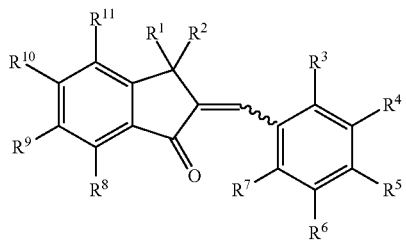

where $R^1$ and $R^2$ independently of each other signify hydrogen or a branched or unbranched alkyl group having from 1 to 12 carbon atoms and
where $R^3$, $R^4$, $R^5$, $R^6$, $R^7$, $R^8$, $R^9$, $R^{10}$ and $R^{11}$ independently of each other signify hydrogen, hydroxy or a branched or unbranched alkyl or alkoxy group having from 1 to 12 carbon atoms.

With the compounds of the formula (I) set out above, the compound has a specific significance, in which $R^1$ and $R^2$ each signify methyl, $R^9$ and $R^{10}$ each signify methoxy and $R^3$, $R^4$, $R^5$, $R^6$, $R^7$, $R^8$ and $R^{11}$ each signify hydrogen. This compound is 2-benzylidene-3,3-dimethyl-5,6-dimethoxy-1-indanone (CAS Nr. 924656-15-3; INCI Title: Benzylidene dimethoxydimethylindanone).

Specific compounds having the formula (I) and the compound which is particularly relevant in the context of the present invention 2-benzylidene-3,3-dimethyl-5,6-dimethoxy-1-indanone are known from the publication WO 2007/128723 A1 (Symrise). They are effective as aryl/hydrocarbon receptor antagonists (Ah receptor antagonist; AhR antagonist). Specific effects, uses and recipes (formulations, preparations, etc.) comprising or relating to a compound having the formula (I) arise from WO 2007/128723 A1.

The compounds having the formula (I) produced by the method according to the invention, in particular the preferred compound 2-benzylidene-3,3-dimethyl-5,6-dimethoxy-1-indanone are present as E or Z isomers or in the form of an E/Z isomer admixture. In the present text in formula drawings, a wavy line is used in order to indicate that the corresponding compound is E or Z configured or a mixture of E and Z isomers is present. The publication WO 2007/128723 A1 discloses in example 1a a method for producing 2-benzylidene-3,3-dimethyl-5,6-dimethoxy-1-indanone. The reaction equation for the synthesis reaction is set out below:

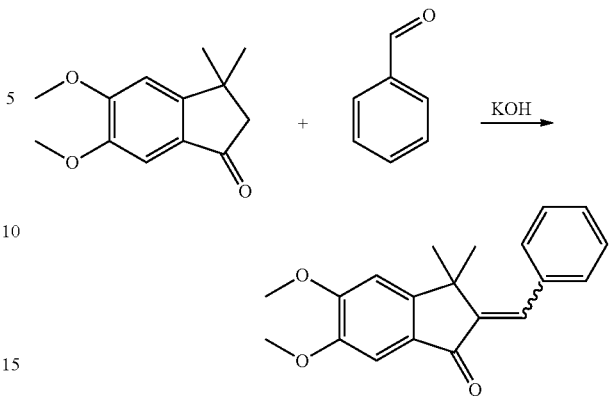

According to example 1 of WO 2007/128723 A1, the compound 3,3-dimethyl-5,6-dimethoxy-1-indanone (first reactant according to the above reaction equation) is added to a suspension of potassium hydroxide in diethylene glycol dimethyl ether. After heating to 80° C., benzaldehyde is added over the course of an hour, and the admixture is stirred for a further 3 hours at the said temperature. In this instance, the 3,3-dimethyl-5,6-dimethoxy-1-indanone is converted with the benzaldehyde. Subsequently, it is cooled to ambient temperature, iced water is added and neutralised by the addition of hydrochloric acid. After extraction with methyl-tert/butylether, the product is recrystallised from methanol. An E/Z isomer admixture is obtained at a yield of 76% of the theoretical quantity. The quantity of potassium hydroxide used according to example 1 of WO 2007/128723 A1 corresponds to approximately 40 mol % with respect to the quantity of 3,3-dimethyl-5,6-dimethoxy-1-indanone used. During our own work for configuring the method according to WO 2007/128723 A1, after crystallisation a product having a proportion of 99.6% of the target product 2-benzylidene-3,3-dimethyl-5,6-dimethoxy-1-indanone and 0.3% of 2-benzyl-3,3-dimethyl-5,6-dimethoxy-1-indanone could be obtained at best (as a by-product), which had a strong yellow colour. It should be noted in this regard that, after the addition of water, as provided for according to WO 2007/128723 A1, another solvent which cannot be mixed with water has to be added in order to extract the product from the aqueous phase. This extraction step involves complexity and costs.

The method disclosed in WO 2007/128723 A1 for producing 2-benzylidene-3,3-dimethyl-5,6-dimethoxy-1-indanone may have been found to be suitable in practice, but still has a range of economical and ecological disadvantages. For instance, according to WO 2007/128723 A1, the educt indanone is dissolved in diethylene glycol methyl ether; however, according to the Globally Harmonized System of Classification and Labelling of Chemicals (GHS), this compound is a so-called CMR material (carcinogenic, mutagenic, toxic in reproduction terms) of category 1B (there are sufficient indications for CMR properties). Particularly for substances which are intended to be used in the cosmetic field, this is critical or unacceptable since it cannot be excluded with sufficient certainty that residual quantities of diethylene glycol dimethyl ether remain in the product (with the main component 2-benzylidene-3,3-dimethyl-5,6-dimethoxy-1-indanone). In addition, the diethylene glycol dimethyl ether is very highly water-soluble so that it reaches the waste water with the water present in the product admixture. The processing of the waste water or the disposal thereof are economically disadvantageous and, in addition, the costs for the diethylene glycol dimethyl ether are themselves considerable, in particular since it cannot be recovered in sufficiently pure form after the reaction. On the whole, therefore, the method disclosed in WO 2007/128723 A1 appears to be uneconomical.

In addition, in the embodiment of the method according to WO 2007/128723 A1, the compound 2-benzyl-3,3-dimethyl-5,6-dimethoxy-1-indanone is produced as an undesirable by-product in a concentration which in most cases is up to approximately 0.5% by weight but which is also more than this in many cases. The compound 2-benzyl-3,3-dimethyl-5,6-dimethoxy-1-indanone has a structure according to the following formula (V):

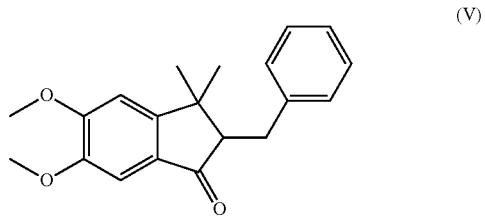 [SMILES: COc1cc2c(cc1OC)C(C)(C)C(Cc1ccccc1)C2=O]

(V)

The by-product (V) consequently differs from the target product (2-benzylidene-3,3-dimethyl-5,6-dimethoxy-1-indanone) only in that it has no dual bond at the 2-position of the 5-ring. The by-product cannot be adequately separated from the target product using conventional physical separation methods, such as distillation or crystallisation, with the result that, in the embodiment of the method according to WO2007/128723 A1, it is always contaminated with considerable quantities of the by-product. In contrast to the target product 2-benzylidene-3,3-dimethyl-5,6-dimethoxy-1-indanone, the by-product 2-benzyl-3,3-dimethyl-5,6-dimethoxy-1-indanone cannot be readily dissolved in cosmetic oils. In our own tests, it has been found that a proportion of 250 ppm (0.025% by weight) of the by-product (V) with respect to the entire mass of a conventional cosmetic formulation already initiates the formation of crystallisation seeds. Cf. in this regard the examples below. However, since cosmetic formulations are generally required to have to be homogeneous, the presence of formulation components with poor solubility in cosmetic oils is generally not acceptable. The presence of the by-product is consequently another disadvantage which is linked with the embodiment of the method according to WO 2007/128723 A1.

Finally, the product produced according to example 1 of WO 2007/128723 A1 or product admixture has a disturbing yellow colouring which indicates the presence (which cannot be identified structurally at this time) of additional by-products having an intense colour. The yellow colouring of the product or the product admixture according to WO 2007/128723 A1 has a disadvantageous effect on the colour of each cosmetic or pharmaceutical product, which is produced with the addition of the product produced according to WO 2007/128723 A1. The yellow colouring of the said product is consequently another significant disadvantage involved in carrying out the method according to WO 2007/128723 A1.

Finally, it should be noted that, according to the embodiment of the method from WO 2007/128723 A1, high quantities of potassium hydroxide are added (as a catalyst base) (approximately 40 mol % with respect to the quantity of indanone derivative used) which, during the processing of the reaction admixture by means of neutralisation with hydrochloric acid leads to considerable salt loads in the waste water. This is another ecological disadvantage.

An object of the present invention was consequently to provide a method which alleviates or preferably completely overcomes at least some or preferably all of the above-mentioned disadvantages of the embodiment of the method according to WO 2007/128723 A1. Preferred methods which are intended to be set out should consequently where possible lead to product admixtures which are not contaminated by diethylene glycol methyl ether, the resulting products preferably being intended to comprise a reduced quantity of the undesirable by-product having the formula (IV)

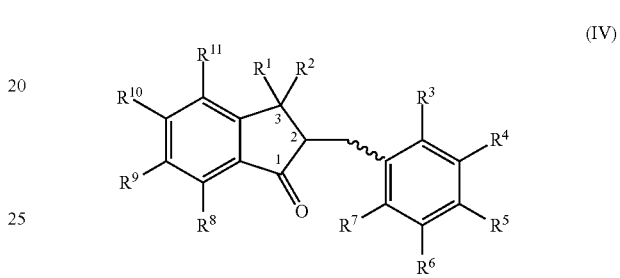

(IV)

and preferably being intended to contain a reduced quantity of the structurally non-identified impurities, which cause the yellow colouring of products according to WO 2007/128723 A1. The by-product having the formula (IV) differs from the compound having the formula (I) in that no dual bonding is present in the 2-position of the 5-ring (cf. the numbering in the 5-ring of the formula (IV)). Other objectives will be appreciated from the following description.

According to the invention, at least some of the above-mentioned objectives are achieved by a method for producing a compound having the formula (I)

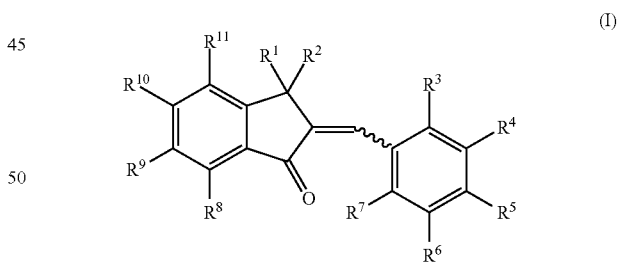

(I)

or an admixture comprising a compound having the formula (I), having the following steps:

dissolving an indanone having the formula (II) in a solvent or in an admixture which contains a solvent, the solvent being selected from the group of solvents which form an azeotrope with water, converting the indanone having the formula (II) with an aromatic aldehyde having the formula (III) in the presence of at least one organic base, according to the drawing:

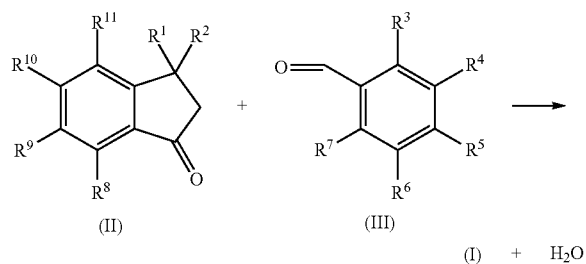

where $R^1$ and $R^2$ independently of each other signify hydrogen or a branched or unbranched alkyl group having from 1 to 12 carbon atoms and
where $R^3$, $R^4$, $R^5$, $R^6$, $R^7$, $R^8$, $R^9$, $R^{19}$ and $R^{11}$ independently of each other signify hydrogen, hydroxy or a branched or unbranched alkyl or alkoxy group having from 1 to 12 carbon atoms and removing water formed from the reaction admixture during the conversion.

Of course, the substituents $R^1$ to $R^{11}$ in formula (I) always have precisely the significance which they have in the formulae (II), (III) and (IV), respectively.

Preferably in the compound having the formula (I) and the educt compounds having the formulae (II) and (III), the substituents $R^1$ and $R^2$ independently of each other signify methyl, ethyl, n-propyl or iso-propyl and the substituents $R^3$, $R^4$, $R^5$, $R^6$, $R^7$, $R^8$, $R^9$, $R^{10}$ and $R^{11}$ signify independently of each other hydrogen, methyl, ethyl, n-propyl, iso-propyl, methoxy, ethoxy, propoxy or butoxy.

In a particularly preferred manner, in the said formulae the substituents $R^1$ and $R^2$ signify methyl and the substituents $R^3$, $R^6$, $R^7$, $R^8$ and $R^{11}$ signify hydrogen and the substituents $R^4$, $R^5$, $R^9$ and $R^{10}$ signify hydrogen, methoxy or n-propoxy independently of each other.

In a quite particularly preferred manner, the substituents $R^1$ and $R^2$ signify methyl, the substituents $R^9$ and $R^{10}$ signify methoxy and the substituents $R^3$, $R^4$, $R^5$, $R^6$, $R^7$, $R^8$ and $R^{11}$ signify hydrogen. As already mentioned, a central notion of the present invention is based on a method for producing 2-benzylidene-3,3-dimethyl-5,6-dimethoxy-1-indanone. This compound is such a compound having the formula (I), in which according to the embodiment which is indicated above as being particularly preferred, $R^1$ and $R^2$ signify methyl, $R^9$ and $R^{10}$ signify methoxy and $R^3$, $R^4$, $R^5$, $R^6$, $R^7$, $R^8$, and $R^{11}$ signify hydrogen.

The general reaction equation relating to the formation of 2-benzylidene-3,3-dimethyl-5,6-dimethoxy-1-indanone is set out below:

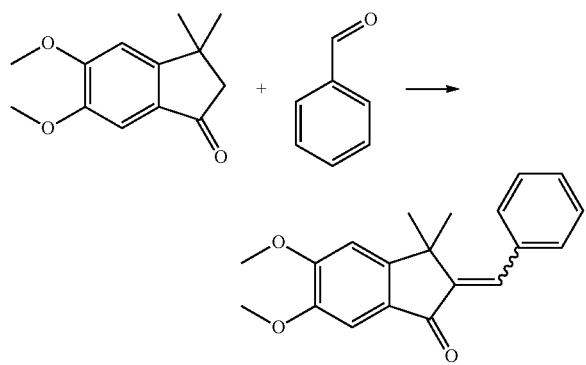

According to the invention, in contrast to the embodiment of the method according to WO 2007/128723 A1, during the conversion the water formed by the reaction step of elimination is removed from the reaction admixture. In our own tests, it has surprisingly been found that with such an embodiment of the method according to the invention, when solvents are used which form an azeotrope with water and when an organic base is used as a catalyst, not only can the yield of the synthesis reaction be significantly increased in comparison with the embodiment of the method according to WO 2007/128723 A1, but the content of by-products (benzyl derivatives; yellow colouring substances) is also significantly reduced. The content of benzyl derivatives which occur as a by-product was regularly so low in our own tests that it was no longer detectable in routine GC examinations.

Preferably, in a method according to the invention, the organic base is selected in such a manner that it transfers the indanone having the formula (II) for conversion with the aldehyde having the formula (III) into the corresponding enolate. This means that the organic base preferably used itself acts as a catalyst for the part-reactions which are taking place (aldol addition and aldol condensation).

Preferably, the organic base is an alcoholate, preferably an alkali metal or alkaline earth metal alcoholate, preferably an alkali metal or alkaline earth metal alcoholate having a branched alcoholate anion.

In a particularly preferred manner, the organic base is selected from the group comprising potassium-tert-butanolate, sodium-tert-butanolate, lithium-tert-butanolate, barium-tert-butanolate, magnesium-tert-butanolate, potassium tert-pentanolate, sodium tert-pentanolate and lithium tert-pentanolate, the organic base preferably being selected from the group comprising sodium-tert-butanolate and potassium tert-butanolate.

When the particularly preferred organic bases are used, it has been found in our own tests that particularly good yields of the respective target product could be achieved, with the quantity of by-products formed being drastically reduced at the same time.

In addition, when the organic bases which are indicated as being particularly preferred are used, a comparatively small amount of these bases can be used, which contributes to alleviating the disadvantages which are set out above and which are connected with the occurrence of the corresponding salts.

As already set out above, in particular when an organic base which is indicated above as being preferred is used, an embodiment of the method is possible in which the quantity of organic base used is comparatively small. Advantageously, the substance quantity ratio of the used quantity of organic base to the used quantity of indanone having the formula (II) is less than 0.50, preferably less than 0.20, preferably less than 0.10, in a particularly preferred manner less than 0.05.

Of course, however, in a method according to the invention a catalytically effective quantity of the organic base is generally used, the organic base preferably being one of the above-mentioned preferred bases. In our own tests, embodiments of the method have been found to be particularly effective in which the substance quantity ratio of the used quantity of organic base to the quantity used of indanone having the formula (II) is greater than 0.005, preferably greater than 0.01, preferably greater than 0.02. Furthermore, the substance quantity ratio of the used quantity of organic base to the quantity used of indanone having the formula (II)

is less than 0.50, preferably less than 0.20, preferably less than 0.10, particularly preferably less than 0.05.

Owing to the use of an appropriate amount of organic base, the quantity of salt which would otherwise be produced by the neutralisation with acid can be reduced; cf. in this regard the notes further above.

Of course, the total quantity of base used advantageously corresponds to the total quantity of organic bases used, that is to say, in addition to the organic base(s) used, no additional bases should be used in the method according to the invention which catalyse the conversion of the indanone having the formula (II) with the aldehyde having the formula (III). The person skilled in the art can determine the quantity of organic base required for the complete conversion of the educts used using simple preliminary tests. For example, the person skilled in the art will to this end gradually increase the quantity of base with the reaction conditions otherwise remaining the same, until no further increase of the yield is achieved.

Preferably, the indanone having the formula (II) and the aromatic aldehyde having the formula (III) are converted without the addition of one or more inorganic bases.

In preferred methods according to the invention, the $pK_s$ value in water of the corresponding acid of the organic base used is greater than 14.0, preferably greater than 14.5, preferably greater than 15.0.

The term a "base" in the context of the present text is intended to be understood to refer to a material which receives protons (proton acceptor).

Preferably, a method according to the invention comprises the following step or the following steps:
removing water formed during the conversion from the reaction admixture by means of azeotropic distillation
and/or
removing water formed during the conversion from the reaction admixture by means of adsorption in a water adsorber, preferably on a molecular sieve.

In this instance, the embodiment of the method in which an azeotropic distillation is carried out is particularly advantageous since this embodiment of the method is particularly advantageous in technical terms. Advantageously, the solvent which is used in the method according to the invention and which forms an azeotrope with water has solubility in water which at 20° C. is less than 20 g of solvent per liter of water, preferably less than 5 g of solvent per liter of water and, in a particularly preferred manner, less than 2 g of solvent per liter of water.

In the context of the present text, solvents which at 20° C. have a solubility in water which is less than 20 g of solvent per liter of water, are intended to be understood to be solvents which dissolve very poorly in water at 20° C.

Preferably, in addition to the solvent which forms an azeotrope with water and which has poor solubility in water in the method according to the invention, no other solvents which form an azeotrope with water are used which have a solubility in water which at 20° C. is greater than 20 g (preferably 5 g, in a particularly preferred manner 2 g) of solvent per liter of water.

Of course, when the above-mentioned compounds which are preferred as an organic base are used in the reaction admixture, alcohols are produced by means of hydrolysis but are not considered in the above sense to be "solvents" of the type in which the indanone having the formula (II) is dissolved.

In a method according to the invention, according to one alternative the indanone having the formula (II) can be dissolved in an admixture containing a solvent, the solvent being selected from the group of solvents which form an azeotrope with water. In addition to the said solvent, which forms an azeotrope with water, other solvent components may be present in the admixture which—considered per se—also form or would form an azeotrope with water. However, in addition to a single solvent which forms an azeotrope with water, the admixture may also comprise other admixture components in dissolved, emulsified or suspended form, which do not form any azeotrope with water. For example, a solvent such as toluol which forms an azeotrope with water may be used in admixture with one or two other organic compounds which form an azeotrope with water or which do not form any azeotrope with water.

If the indanone having the formula (II) is dissolved in an admixture containing a solvent, the solvent being selected from the group of solvents which form an azeotrope with water, it is advantageous for the admixture to completely comprise or to comprise more than 50% by weight (preferably more than 80% by weight) of this solvent which forms an azeotrope with water.

Particularly preferred are methods according to the invention in which the solvent which forms an azeotrope with water is selected from the group comprising benzol, toluol, xylol, n-hexane, n-heptane, cyclohexane, methylcyclohexane and tetrachloromethane, preferably from the group comprising toluol and xylol.

According to the invention, the indanone having the formula (II) is dissolved in a solvent or in an admixture which contains a solvent.

If the indanone having the formula (II) is dissolved in a (single) solvent (that is to say, not in an admixture), this solvent is preferably selected from the above-mentioned group; preferably the solvent is toluol or xylol.

If the indanone having the formula (II) is dissolved in an admixture which contains a solvent, the or at least one of the solvent(s) in the admixture is/are preferably selected from the above-mentioned group; the solvent is preferably toluol or xylol.

If the indanone having the formula (II) is dissolved in an admixture containing a solvent, the admixture preferably completely comprises or comprises more than 50% by weight (preferably more than 80% by weight) of one or more solvents which are selected from the above-mentioned group; preferably, the admixture completely comprises toluol and xylol or more than 50% by weight (preferably more than 80% by weight) of toluol and/or xylol.

The use of a solvent which dissolves very poorly in water at 20° C. but which forms an azeotrope with water enables, when an azeotropic distillation is carried out (see above in this regard), the reaction water to be reliably removed from the reaction admixture, but enables the solvent which is also separated during the azeotropic distillation to be recovered (for example, using a conventional water separator) and to be returned to the reaction admixture).

In a method according to the invention, the substance quantity ratio of the used quantity of indanone having the formula (II) to the used quantity of aldehyde having the formula (III) is preferably in the range from 0.6 to 1.4, preferably in the range from 0.8 to 1.0. It has been found that, with a substance quantity ratio >1.4, the reaction sequence is comparatively uneconomical. The indanone having the formula (II) used in excess must be removed from the product admixture after the reaction. An excess of indanone having the formula (II) is generally for economical reasons less advantageous than an excess of aldehyde having the formula (III). With a high content of indanone having the formula (II) in the product admixture, the complexity required to obtain the product with sufficient purity increases. To this end, the product in some circumstances has to be cleaned several times (for example, recrystallised). The indanone having the formula (II) which is used in excess and recovered after the cleaning operation is generally not present in a sufficiently pure form and therefore cannot be used again without further processing.

After successful conversion, in a method according to the invention a product admixture is present which has developed from the reaction admixture initially present. Advantageously, the product admixture is processed in a method according to the invention. Preferably, in order to process the product admixture present after successful conversion, the following steps are carried out:

neutralising the product admixture,
distilling solvent from the neutralised product admixture, preferably distilling the product;
subsequently preferably recrystallising the product.

In this manner, a product of high purity is obtained. Owing to the recrystallisation of the product, a particularly high degree of purity is achieved.

In the interests of an economically advantageous embodiment of the method, the conversion of the indanone having the formula (II) with the aromatic aldehyde having the formula (III) is carried out in the preferred method according to the invention until a conversion of at least >70%, preferably >80%, in a particularly preferred manner >90% is achieved. The conversion is based on the used quantity of educt which is used in insufficient amounts. If the indanone having the formula (II) and the aromatic aldehyde having the formula (III) are used in an equimolar quantity, the conversion is based on the used quantity of indanone having the formula (II).

The person skilled in the art can follow the progress of the reaction in conventional manner using gas chromatography; in order to determine the conversion at a specific time, the person skilled in the art will remove a sample from the reaction admixture and, after corresponding calibration, will carry out a gas-chromatographic examination in conventional manner.

In order to achieve particularly outstanding method results, that is to say, in particular to achieve particularly pure products, in preferred methods according to the invention, the following steps are carried out before the conversion of the indanone having the formula (II) with the aromatic aldehyde having the formula (III):

washing the solution present after the dissolution of the indanone having the formula (II) with an aqueous alkaline solution and separating the aqueous phase after washing,
preferably washing the resulting solution with a salt solution, preferably with an NaCl solution,
preferably removing the residual water remaining after washing from the organic phase, preferably by means of azeotropic distillation.

This preferred embodiment of a method according to the invention leads to a product which is particularly pure and which is in particular almost free from the by-products discussed above, which differ from the desired target product only in that it has no dual-bond with carbon in the 2-position of the 5-ring of the formula (II). This is particularly relevant for methods according to the invention for producing 2-benzylidene-3,3-dimethyl-5,6-dimethoxy-1-indanone. Conventionally, the production of the 3,3-dimethyl-5,6-dimethoxy-1-indanone used in the preferred embodiment according to the invention from the educts veratrol (1,2-dimethoxybenzol) and 3,3-dimethylacrylic acid is carried out in the presence of large quantities of polyphosphoric acid. In spite of thorough preparation, small quantities of acid are generally still present in the 3,3-dimethyl-5,6-dimethoxy-1-indanone. In the preferred embodiment according to the invention, which involves the washing of the solution present after the dissolution of the 3,3-dimethyl-5,6-dimethoxy-1-indanone (as described, generally contaminated with acid) in aqueous alkaline solution and separating the aqueous phase after the washing, the formation of the 2-benzyl-3,3-dimethyl-5,6-dimethoxy-1-indanone (as a by-product) is drastically reduced. In addition, a product results which has only an extremely slight yellow colouring, cf. in this regard, the examples further below.

According to the above, a particularly preferred method according to the invention comprises the following steps:

providing or producing an indanone having the formula (II) and an aldehyde having the formula (III) as defined above,
dissolving the indanone in the solvent or in an admixture containing the solvent so that a solution of the indanone results,
washing the solution present after the dissolution of the indanone having the formula (II) with an aqueous alkaline solution and separating the aqueous phase after washing,
preferably washing the resulting solution with a salt solution, preferably with an NaCl solution,
preferably removing residual water remaining after the washing from the organic phase, preferably by means of azeotropic distillation,
adding the organic base and preferably gradually the aldehyde to the solution of the indanone from which residual water has preferably been removed so that a reaction admixture is formed, in which the indanone having the formula (II) is converted with the aromatic aldehyde having the formula (III),
removing water produced during the conversion from the reaction admixture by means of azeotropic distillation,
neutralising the product admixture present after successful conversion,
distilling solvent from the neutralised product admixture, preferably distilling the product,
subsequently preferably recrystallising the product.

According to the above, 3,3-dimethyl-5,6-dimethoxy-1-indanone is preferably used as the indanone having the formula (II) and benzaldehyde is preferably used as the aromatic aldehyde having the formula (III).

In the preferred method according to the invention, during the processing after the neutralisation of the product admixture and the distillation of solvent from the neutralised product admixture, the recrystallisation of the resulting product is preferably carried out. The recrystallisation of the product will in this instance preferably be carried out from a solvent in which the product dissolves less readily at 20° C. than at the boiling temperature of the solvent, preferably from an alkanol having from 1 to 4 carbon atoms, in a particularly preferred manner from methanol, ethanol, propanol or an admixture of two or more of these alkanols. In a quite particularly preferred manner, the recrystallisation is from ethanol. It has been found that, when the said alkanols are used (in particular ethanol), particularly good recrystallisation results can be achieved. Of course, before the step of recrystallisation, the solvents which are still present from previous process steps are removed in the most complete manner possible.

The person skilled in the art will preferably optimise the previously discussed method parameters with reference to conventional preliminary tests in such a manner that he obtains particularly pure products. In particular, he will adjust or select the following method parameters in the manner set out above:

The solvent used is preferably selected in such a manner that it forms an azeotrope with water, but is very poorly soluble in water at 20° C. It is consequently possible to remove the water formed during the reaction by means of azeotropic distillation and to return the solvent.

The temperature adjusted during the reaction is preferably selected in such a manner that the solvent used boils so that the water formed during the reaction can be removed by means of azeotropic distillation.

The ratio of the quantity of the indanone having the formula (II) to the used quantity of aldehyde having the formula (III) is preferably adjusted in such a manner that only small quantities of the educts used remain in the product admixture.

The organic base used is preferably selected in such a manner that it transfers the indanone having the formula (II) for conversion with the aldehyde having the formula (III) into the corresponding enolate.

The ratio of the used quantity of the organic base to the quantity used of indanone having the formula (II) is preferably adjusted in such a manner that the quantity of organic base required for the complete conversion is achieved, but at the same time as little of the organic base as possible is used.

The solvent used for the recrystallisation is preferably selected in such a manner that all the components of the product admixture can be dissolved in the boiling heat of the solvent for the recrystallisation after the distillation of the solvent used for the reaction but, during cooling, the compound having the formula (I) crystallises out as completely as possible, whilst all the other components remain in solution.

On the whole, the person skilled in the art thus arrives at a particularly preferred method according to the invention for producing a compound having the formula (I) or an admixture comprising a compound having the formula (I), the method conditions being adjusted in such a manner that the substance quantity ratio of the produced quantity of the compound having the formula (I) to the quantity of the compound having the formula (IV) which may be produced as a by-product

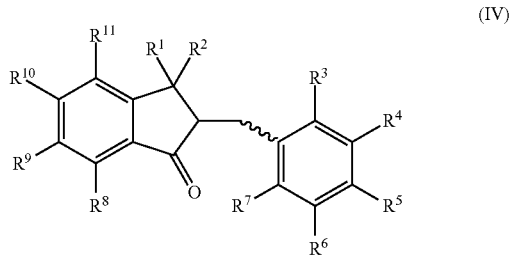

(IV)

in which the significance of the groups $R^1$, $R^2$, $R^3$, $R^4$, $R^5$, $R^6$, $R^7$, $R^8$, $R^9$, $R^{10}$, $R^{11}$ and $R^{12}$ is the same as the significance of the groups having the same designation in the compound having the formula (I),
is greater than 50, preferably greater than 100, preferably greater than 1000.

The present invention also relates to an admixture comprising a compound of the formula (I) as defined above with respect to the method according to the invention, optionally a corresponding compound having the formula (IV) as defined above (that is to say, a compound having the formula (IV) which differs only owing to the absence of a dual bond to the carbon in the 2-position of the 5-ring having the formula (II) from the compound having the formula (I) contained in the admixture), the substance quantity ratio of the total quantity of the compound having the formula (I) to the total quantity of the compound having the formula (IV), which quantity may be present, being greater than 50, preferably greater than 100, preferably greater than 1000, optionally a substance which colours the admixture yellow, a quantity of solvent selected from the group of solvents which form an azeotrope with water and which dissolve very poorly in water at 20° C., and optionally other components, which can be produced in accordance with a method according to the invention as defined above.

All the statements made above in relation to the method according to the invention apply to the admixture according to the invention and the components contained in the admixture. This applies in particular to the solvents selected.

The person skilled in the art can distinguish the admixture according to the invention with reference to the presence of a residual quantity of solvent, which forms an azeotrope with water, but which can be dissolved very poorly in water at 20° C., from admixtures which are already known from the prior art.

Although it is advantageous for cosmetic practice when an admixture which comprises a compound having the formula (I) comprises only very small quantities or no quantities of the said solvents, it has been found in our own tests that, in the method according to the invention, even when a recrystallisation is carried out, (extremely small) quantities of solvent still remain in the product admixture. Typical quantities of solvent which remain in the product admixture even after recrystallisation are smaller than 0.01% by weight, with particularly careful preparation in many cases less than 0.001% by weight. However, the remaining quantity of solvent is generally greater than 0.0001% by weight so that the product admixture generally contains the solvent in a quantity which is in the range from 0.0001% by weight to 0.01% by weight, preferably in the range from 0.0001% by weight to 0.001% by weight with respect to the total mass of the product admixture.

In a preferred admixture according to the invention, the proportion of the compound having the formula (I) is more than 99.5% by weight, preferably more than 99.9% by weight, in a particularly preferred manner more than 99.99% by weight, with respect to the total mass of the admixture.

The present invention also relates to preferred admixtures according to the invention, which are cosmetic or pharmaceutical formulations. Such an admixture according to the invention is preferably provided for use as a skin protection means, light protection means and/or AhR antagonist.

The present invention also relates to a method for producing a skin protection means, light protection means or a compound with AhR antagonistic action, comprising the following steps:

producing a compound having the formula (I) according to a method according to the invention or preparing an admixture according to the invention;

mixing the compound produced or the admixture prepared with cosmetic or pharmaceutical auxiliary agents.

The invention will be explained in detail below with reference to examples.

Method for Determining L*a*b Colour Values

The L*a*b colour values are determined in accordance with DIN EN ISO 11664-4:2011-07. The measurements are carried out with a Lico-300 device from the company Hach Lange Düsseldorf. Only L values established are set out below. The L value reflects the brightness of the sample. An L value of 100 corresponds to a white sample, an L value of 0 corresponds to a black sample.

COMPARISON EXAMPLE 1

(cf. WO2007/128723 A1, example 1); production of 2-benzylidene-3,3-dimethyl-5,6-dimethoxy-1-indanone COMPARISON EXAMPLE 1a Recrystallisation from Methanol 0.17 mol of solid potassium hydroxide were suspended in 100 g of diethylene glycol dimethyl ether and 0.40 mol of 3,3-dimethyl-5,6-dimethoxy-1-indanone were added. The admixture was heated to 80° C. with agitation. Within an hour, 0.61 mol of benzaldehyde were added and the solution was stirred for a further three hours at 80° C. For processing, the solution was cooled to ambient temperature, 400 g of iced water was added and neutralised with 30 g of 10% aqueous hydrochloric acid solution. After extraction with 400 g of methyl-tert-butylether, the product was recrystallised from methanol. 96.2 g was obtained (78% by weight of the theoretical quantity with respect to the 3,3-dimethyl-5,6-dimethoxy-1-indanone) of a yellow solid. According to routine GC examinations, the product had a purity of 99.6% by weight (2-benzylidene-3,3-dimethyl-5,6-dimethoxy-1-indanone) and contained 0.3% by weight of 2-benzyl-3,3-dimethyl-5,6-dimethoxy-1-indanone and 0.1% of additional impurities. An L*a*b colour measurement was carried out on the product produced. The L-value of the product was 88.58.

COMPARISON EXAMPLE 1b

Recrystallisation from Ethanol

With an alternative recrystallisation from ethanol, almost identical results were achieved.

COMPARISON EXAMPLE 2

Production of 2-benzylidene-3,3-dimethyl-5,6-dimethoxy-1-indanone

COMPARISON EXAMPLE 2a

Recrystallisation from Methanol

The procedure in comparison example 2a corresponds to the procedure according to comparison example 1a, but 100 g of diethylene glycol diethyl ether were used as the solvent instead of 100 g of diethylene glycol dimethyl ether.

90.0 g (73% by weight of the theoretical quantity with respect to 3,3-dimethyl-5,6-dimethoxy-1-indanone) of a yellow solid material were obtained. The product had according to GC examinations a purity of 99.6% by weight (2-benzylidene-3,3-dimethyl-5,6-dimethoxy-1-indanone) and contained 0.3% by weight of 2-benzyl-3,3-dimethyl-5,6-dimethoxy-1-indanone and 0.1% by weight of other impurities.

COMPARISON EXAMPLE 2b

Recrystallisation from Ethanol

With an alternative recrystallisation from ethanol, almost identical results were achieved.

COMPARISON EXAMPLE 3

Production of 2-benzylidene-3,3-dimethyl-5,6-dimethoxy-1-indanone

COMPARISON EXAMPLE 3a

Recrystallisation from Methanol

The procedure in comparison example 3a corresponds to the procedure according to comparison example 2a, but 10 mmol of potassium hydroxide were used. Only 2 g of a 10% aqueous hydrochloric acid solution were used in order to neutralise the solution. 123 g of a yellow educt product admixture were obtained. Using GC measurements, it was possible to establish that the yellow educt product admixture contained 19.7 g (16% by weight of the theoretical quantity with respect to the 3,3-dimethyl-5,6-dimethoxy-1-indanone) of the product.

COMPARISON EXAMPLE 3b

Recrystallisation from Ethanol

With an alternative recrystallisation from ethanol, almost identical results were achieved.

COMPARISON EXAMPLE 4

Production of 2-benzylidene-3,3-dimethyl-5,6-dimethoxy-1-indanone

COMPARISON EXAMPLE 4a

Recrystallisation from Methanol

The procedure in comparison example 4a corresponds to the procedure according to comparison example 2a, but 0.7 g (12 mmol) of potassium hydroxide were used. 100 g of toluol were used as a solvent in place of 100 g of diethylene glycol diethyl ether. Only 2 g of a 10% aqueous hydrochloric acid solution were used in order to neutralise the solution. 21.0 g (17% by weight of the theoretical quantity with respect to the 3,3-dimethyl-5,6-dimethoxy-1-indanone) of a yellow solid product were obtained.

COMPARISON EXAMPLE 4b

Recrystallisation from Ethanol

With an alternative recrystallisation from ethanol, almost identical results were achieved.

EXAMPLE 1

Production of 2-benzylidene-3,3-dimethyl-5,6-dimethoxy-1-indanone

EXAMPLE 1a

Recrystallisation from Methanol 89 g (0.40 mol) of 3,3-dimethyl-5,6-dimethoxy-1-indanone which was produced in conventional manner were dissolved in 180 g of toluol. This solution was washed with 60 mL of a 5% aqueous solution of potassium hydroxide and then twice, each time with 50 mL of a 10% aqueous cooking salt solution. Subsequently, the organic solution was cleaned of residual water in an azeotropic manner in a water separator. Approximately 80 g of toluol (upper phase) and approximately 2 g of water (lower phase) accumulated in the water separator.

1.1 g (10 mmol) of potassium-tert-butanolate were added to the dry solution of the 3,3-dimethyl-5,6-dimethoxy-1-indanone in toluol; the resulting admixture was stirred under reflux (approximately 110° C.). Within 1 hour, 65 g (0.61 mol) of benzaldehyde were added and the solution was stirred for a further 3 hours at said temperature. During the entire reaction time, the resultant reaction water produced was distilled in an azeotropic manner by means of a water separator. For processing, the solution was cooled to ambient temperature, 400 g of iced water was added and the solution was neutralised with 3 g of a 10% aqueous hydrochloric acid solution. The remaining organic phase was washed with 100 g of a 10% aqueous cooking salt solution, the remaining solution was distilled. Subsequently, the raw product was distilled by means of a short path distillation installation at a pressure of approximately 1 mbar and a temperature of approximately 170° C. After crystallisation of the distillate from methanol, 82 g (66% of the theoretical quantity with respect to the 3,3-dimethyl-5,6-dimethoxy-1-indanone) of the 2-benzylidene-3,3-dimethyl-5,6-dimethoxy-1-indanone were obtained as a bright yellow solid. The purity of the product was >99.9% by weight. The by-product 2-benzyl-3,3-dimethyl-5,6-dimethoxy-1-indanone observed in the comparison examples could not be detected by means of routine GC examinations. An L*a*b colour measurement was carried out on the product produced. The L-value of the product was 94.09.

EXAMPLE 1b

Recrystallisation from Ethanol

With an alternative recrystallisation from ethanol, almost identical results were achieved.

EXAMPLE 2

Production of 2-benzylidene-3,3-dimethyl-5,6-dimethoxy-1-indanone

EXAMPLE 2a

Recrystallisation from Methanol

The procedure in example 2a corresponds to the procedure according to example 1a, but a distillation of the raw product was dispensed with. After crystallisation of the raw product from methanol, 86 g (69% of the theoretical quantity with respect to the 3,3-dimethyl-5,6-dimethoxy-1-indanone) of the 2-benzylidene-3,3-dimethyl-5,6-dimethoxy-1-indanone were obtained as a bright yellow solid. The purity of the product was >99.9% by weight. The by-product 2-benzyl-3,3-dimethyl-5,6-dimethoxy-1-indanone observed in the comparison examples (compound having the formula (V)) could not be detected by means of routine GC examinations. An L*a*b colour measurement was carried out on the product produced. The L-value of the product was 90.15.

EXAMPLE 2b

Recrystallisation from Ethanol

With an alternative recrystallisation from ethanol, almost identical results were achieved.

EXAMPLE 3

Examination of the Crystallisation in Emulsion

According to the indications in the following Table 1, two cosmetic formulations were produced as emulsions [E(I) and E (II)]. The product from example 1a contained pure 2-benzylidene-3,3-dimethyl-5,6-dimethoxy-1-indanone and was used in the emulsion E(I). For the emulsion E(II), 2-benzylidene-3,3-dimethyl-5,6-dimethoxy-1-indanone from example 1a was used, but it was contaminated with benzyl-3,3-dimethyl-5,6-dimethoxy-1-indanone in such a manner that a 5% by weight contamination was present, with respect to the total mass of the contaminated product.

The emulsions were covered and left to stand at ambient temperature for 3 days. Subsequently, the emulsions were examined under a microscope. Emulsion E(I) had no crystals. In emulsion E(II), crystal seeds having a size of from 4 to 7 μm were able to be observed.

This means that a proportion of from 250 ppm (0.025% by weight) of the by-product (benzyl-3,3-dimethyl-5,6-dimethoxy-1-indanone) already initiates the formation of crystallisation seeds in the cosmetic formulation, whilst a formulation free from by-products has no crystallisation.

TABLE 1

Recipe of the cosmetic formulation used for the crystallisation tests:

| Phase | Raw material | INCI | E(I) % by wt. | E(II) % by wt. |
|---|---|---|---|---|
| A | Water dem | Aqua | 84.15 | 84.15 |
|  | Symdiol 68 | 1,2-hexanediol, Gaprylyl Glycol | 0.60 | 0.60 |
|  | SymMoillent W/S | Trideceth-9, PEG-5 Isononanoate, Aqua | 0.50 | 0.50 |
|  | Glycerin 85% | Glycerin | 1.00 | 1.00 |
|  | Hydrolite 5 | 1,2-pentylene glycol | 1.00 | 1.00 |

TABLE 1-continued

Recipe of the cosmetic formulation used for the crystallisation tests:

| Phase | Raw material | INCI | E(I) % by wt. | E(II) % by wt. |
|---|---|---|---|---|
| B | PCL Liquid 100 | Cetearyl Octanoate | 3.00 | 3.00 |
| | Lanette O | Cetearyl Alcohol | 2.00 | 2.00 |
| | Product from example 1a | Benzylidene Dimethoxydimethylindanone | 0.50 | — |
| | Product from example 1a replaced with 5% by weight benzyl-3,3-dimethyl-5,6-dimethoxy-1-indanone | Benzylidene Dimethoxydimethylindanone; | — | 0.50 |
| | Pemulen TR1 | Acylates/C10-30Alkyl Acrylate Crosspolymer | 0.20 | 0.20 |
| | Carbopol Ultrez-21 | Acylates/C10-30Alkyl Acrylate Crosspolymer | 0.05 | 0.05 |
| | Paraffin oil 5° | Mineral Oil | 3.00 | 3.00 |
| | Dragoxat 89 | Ethylhexyl Isononanoate | 3.00 | 3.00 |
| | Abil 350 | Dimethicone | 0.50 | 0.50 |
| C | NaOH, 10% aq. | Sodium Hydroxide | 0.50 | 0.50 |
| | Total | | 100.00 | 100.00 |

The invention claimed is:

1. Method for the manufacture of a compound of formula (I) having a purity of at least 99.9% comprising:

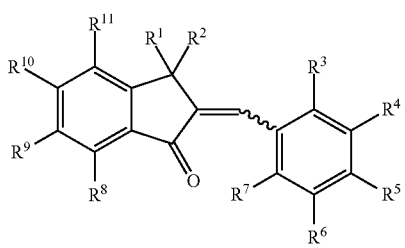

dissolving an indanone of formula (II) in a solvent or in a mixture containing a solvent that forms an azeotrope with water and has a solubility that is less than 20 g of solvent per liter of water at 20° C., conversion of the indanone of formula (II) with an aromatic aldehyde of formula (III) in the presence of at least one organic base that is an alkali metal or alkaline earth metal alcoholate with a branched alcoholate anion, according to the scheme

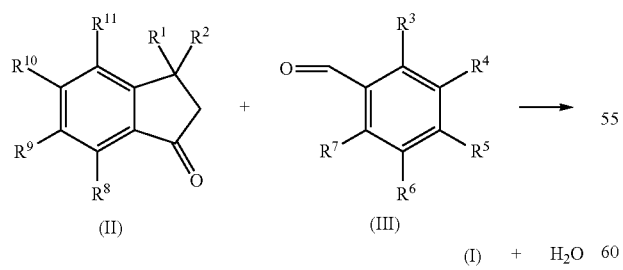

wherein $R^1$ and $R^2$ represent, independently of each other, hydrogen or a branched or unbranched alkyl group with 1 to 12 carbon atoms, respectively, $R^3$, $R^4$, $R^5$, $R^6$, $R^7$, $R^8$, $R^9$, $R^{10}$ and $R^{11}$ represent, independently of each other, hydrogen, hydroxy or a branched or unbranched alkyl or alkoxy group with 1 to 12 carbon atoms, respectively, and the molar ratio of the used amount of organic base to the used amount of indanone of formula (II) is smaller than 0.05, and removal of the generated water from the reaction mixture during the conversion.

2. Method according to claim 1, wherein
$R^1$ and $R^2$ represent, independently of each other, methyl, ethyl, n-propyl or iso-propyl, respectively, and $R^3$, $R^4$, $R^5$, $R^6$, $R^7$, $R^8$, $R^9$, $R^{10}$ and $R^{11}$ represent, independently of each other, hydrogen, methyl, ethyl, n-propyl, iso-propyl, methoxy, ethoxy, propoxy or butoxy, respectively.

3. Method according to claim 1, wherein the molar ratio of the used amount of indanone of formula (II) to the used amount of aldehyde of formula (III) is in the range of 0.6 to 1.4.

4. Method according to claim 1, further comprising:
removal of the water that is generated during the conversion from the reaction mixture by means of azeotropic distillation and/or
removal of the water that is generated during the conversion from the reaction mixture by means of adsorption to a water adsorber.

5. Method according to claim 1, wherein the solvent that forms an azeotrope with water is selected from the group consisting of benzene, toluene, xylene, n-hexane, n-heptane, cyclohexane, methylcyclohexane and carbon tetrachloride.

6. Method according to claim 1, comprising the following additional steps for treatment of an existing product mixture once conversion has taken place:
neutralisation of the product mixture,
removal of the solvent by distillation from the neutralised product mixture, and
subsequently, recrystallisation of the product.

7. Method according to claim 1 with the following step before the conversion of the indanone of formula (II) with the aromatic aldehyde of formula (III):
washing of the solution that is present after dissolving of the indanone of formula (II) with an aqueous, alkaline solution and separation of the aqueous phase after washing.

8. Method according to claim 1 with the following steps:
provision or production of an indanone of formula (II) and of an aldehyde of formula (III),
dissolving of the indanone in the solvent or in a mixture containing the solvent so as to achieve a solution of the indanone,
washing of the solution that is present after dissolving of the indanone of formula (II) with an aqueous, alkaline solution and separation of the aqueous phase after washing,
addition of the organic base and of the aldehyde to the solution of the indanone, so that a reaction mixture is formed in which the indanone of formula (II) reacts with the aromatic aldehyde of formula (III),
removal of the water that is generated during the conversion from the reaction mixture by means of azeotropic distillation,
neutralisation of the product mixture that is present once the conversion has taken place,
removal of the solvent by distillation from the neutralised product mixture, and
recrystallisation of the product.

9. Method according to claim 1, wherein the process conditions are adjusted such that the molar ratio of the produced amount of the compound of formula (I) to
the amount of the compound of formula (IV) that has been produced as side-product, where appropriate,

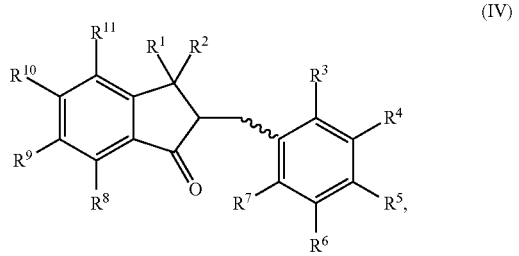

(IV)

in which the denotation of the groups $R^1$, $R^2$, $R^3$, $R^4$, $R^5$, $R^6$, $R^7$, $R^8$, $R^9$, $R^{10}$, $R^{11}$ and $R^{12}$ is the same as the denotation of the groups termed equally in the compound of formula (I),
is larger than 50.

10. Method for the manufacture of a compound of formula (I) having a purity of at least 99.9% comprising:

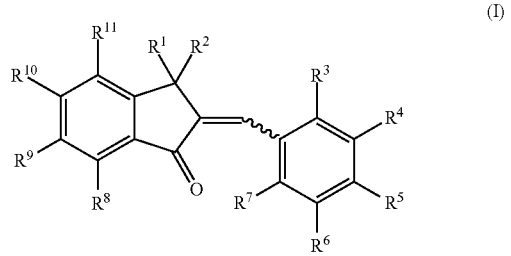

(I)

dissolving an indanone of formula (II) in a solvent that forms an azeotrope with water and has a solubility of less than 20 g of solvent per liter of water at 20° C.,
converting the indanone of formula (II) with an aromatic aldehyde of formula (III) in the presence of at least one organic base selected from the group consisting of potassium tert-butylate, sodium tert-butylate, lithium tert-butylate, barium tert-butylate, magnesium tert-bu-tylate, potassium tert-pentylate, sodium tert-pentylate and lithium tert-pentylate, according to the scheme

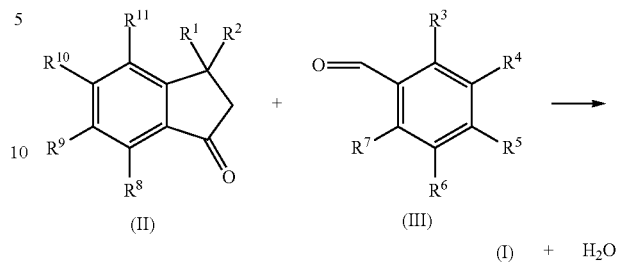

(I) + $H_2O$ wherein $R^1$ and $R^2$ represent, independently of each other, hydrogen or a branched or unbranched alkyl group with 1 to 12 carbon atoms,
$R^3$, $R^4$, $R^5$, $R^6$, $R^7$, $R^8$, $R^9$, $R^{10}$ and $R^{11}$ represent, independently of each other, hydrogen, hydroxy or a branched or unbranched alkyl or alkoxy group with 1 to 12 carbon atoms, and
the molar ratio of the used amount of organic base to the used amount of indanone of formula (II) is smaller than 0.05, and
removing the water generated during the conversion.

11. Method according to claim 10, wherein
$R^1$ and $R^2$ represent, independently of each other, methyl, ethyl, n-propyl or iso-propyl, and
$R^3$, $R^4$, $R^5$, $R^6$, $R^7$, $R^8$, $R^9$, $R^{10}$ and $R^{11}$ represent, independently of each other, hydrogen, methyl, ethyl, n-propyl, iso-propyl, methoxy, ethoxy, propoxy or butoxy.

12. Method according to claim 10, wherein the molar ratio of the indanone of formula (II) to the aldehyde of formula (III) is in the range of 0.6 to 1.4.

13. Method according to claim 10, wherein the water is removed by azeotropic distillation and/or by adsorption to a water absorber.

14. Method according to claim 10, wherein the solvent that forms an azeotrope with water is selected from the group consisting of benzene, toluene, xylene, n-hexane, n-heptane, cyclohexane, methylcyclohexane and carbon tetrachloride.

15. Method according to claim 10, wherein the solvent that forms an azeotrope with water is toluene and/or xylene.

16. Method for the manufacture of a compound of formula (I) having a purity of at least 99.9% comprising:

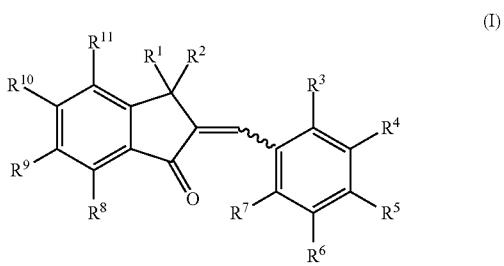

(I)

dissolving an indanone of formula (II) in a solvent that forms an azeotrope with water and has a solubility less than 20 g of solvent per liter of water at 20° C., wherein the solvent is selected from the group consisting of toluene and/or xylene, converting the indanone of formula (II) with an aromatic aldehyde of formula (III) in the presence of at least one organic base selected from the group consisting of potassium tert-butylate, sodium tert-butylate, lithium tert-butylate, barium tert-butylate, magnesium tert-butylate, according to the scheme

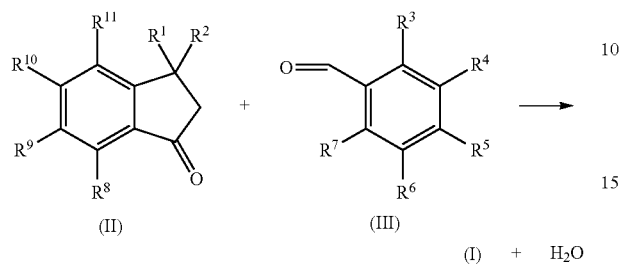

(I) + H$_2$O wherein R$^1$ and R$^2$ represent, independently of each other, hydrogen or a branched or unbranched alkyl group with 1 to 12 carbon atoms, R$^3$, R$^4$, R$^5$, R$^6$, R$^7$, R$^8$, R$^9$, R$^{10}$ and R$^{11}$ represent, independently of each other, hydrogen, hydroxy or a branched or unbranched alkyl or alkoxy group with 1 to 12 carbon atoms, and the molar ratio of the used amount of organic base to the used amount of indanone of formula (II) is smaller than 0.05, and removing the water generated during the conversion.

\* \* \* \* \*